[54] RAPID ASPIRATION SYSTEM FOR CULTURE MEDIA

[75] Inventor: Charles J. Homer, Spring Valley, Calif.

[73] Assignee: Dynasciences Corporation, Los Angeles, Calif.

[21] Appl. No.: 917,714

[22] Filed: Jun. 21, 1978

[51] Int. Cl.² .............................................. C12M 3/00
[52] U.S. Cl. ................................... 435/284; 435/292; 435/297; 435/298; 422/100
[58] Field of Search ...................... 195/127, 142, 139; 422/100; 23/230 B; 435/284, 292, 297, 298

[56] References Cited

U.S. PATENT DOCUMENTS

| | | | |
|---|---|---|---|
| 3,568,735 | 3/1971 | Lancaster | 422/100 X |
| 3,759,667 | 9/1973 | Bannister et al. | 422/100 X |
| 3,772,154 | 11/1973 | Isenberg et al. | 23/230 B X |
| 3,844,896 | 10/1974 | Sharpe | 195/139 |
| 3,992,265 | 11/1976 | Hansen | 195/127 |
| 4,125,436 | 11/1978 | Liner | 195/127 |
| 4,142,668 | 3/1979 | Lee | 422/100 X |

Primary Examiner—R. B. Penland
Attorney, Agent, or Firm—Donald E. Nist

[57] ABSTRACT

The improved system of the present invention comprises a hand manipulatable first manifold comprising a hollow housing and a plurality of stubs connected to said housing at spaced intervals, extending outwardly from said housing and defining openings communicating with the interior of the housing. The stubs have at their free outer ends removable suction cups having central openings in communication with the stub openings. This manifold also includes suction means in the form of tubing connected to the hollow handle portion of the housing for providing suction to the housing, and suction-relieving means in the form of a hand-openable closure releasably sealing an opening in the handle. This manifold permits the simultaneous removal of the covers from a plurality of petri dishes or the like culture-containing reservoirs, by means of the suction cups.

A second manifold is provided which also can be hand held and which comprises a hollow housing having a plurality of aspiration conduits connected to the housing at spaced intervals, extending outwardly from the housing and communicating with the interior of the housing. The aspiration conduits terminate in removable pipettes for aspirating culture media from the reservoirs once the covers have been removed by the first manifold. The number of pipettes is equal to the number of suction cups and the spatial arrangement of the pipettes is the same as that of the cups.

5 Claims, 2 Drawing Figures

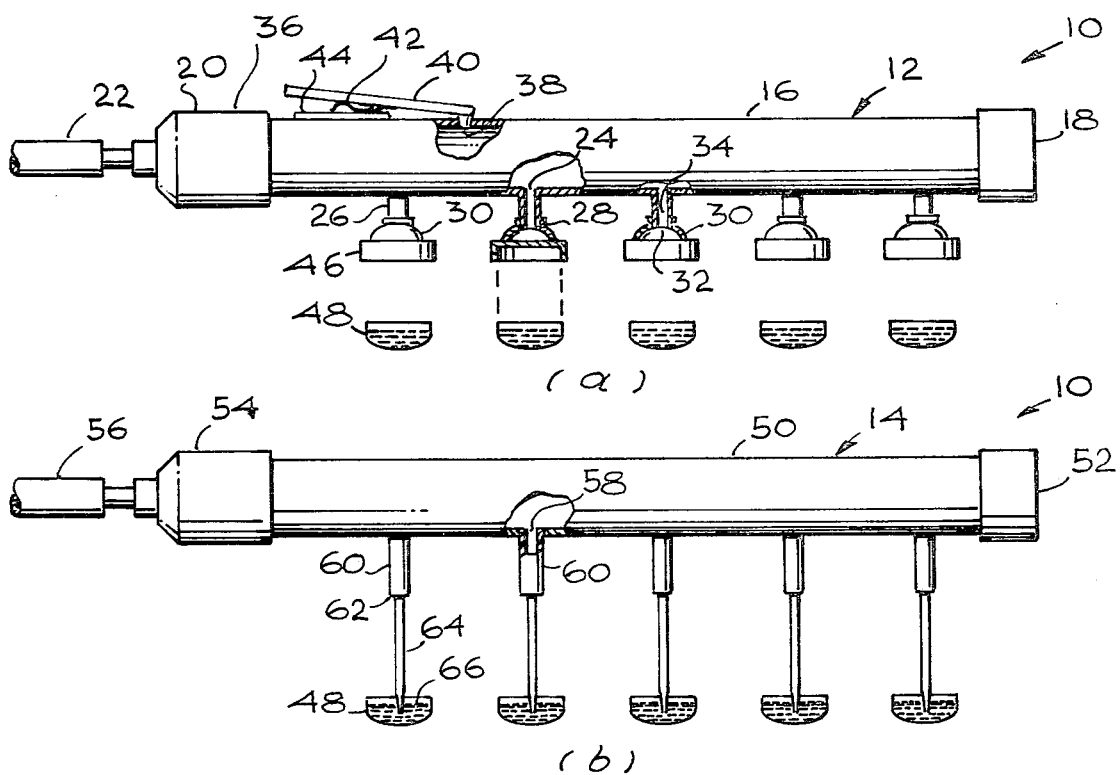
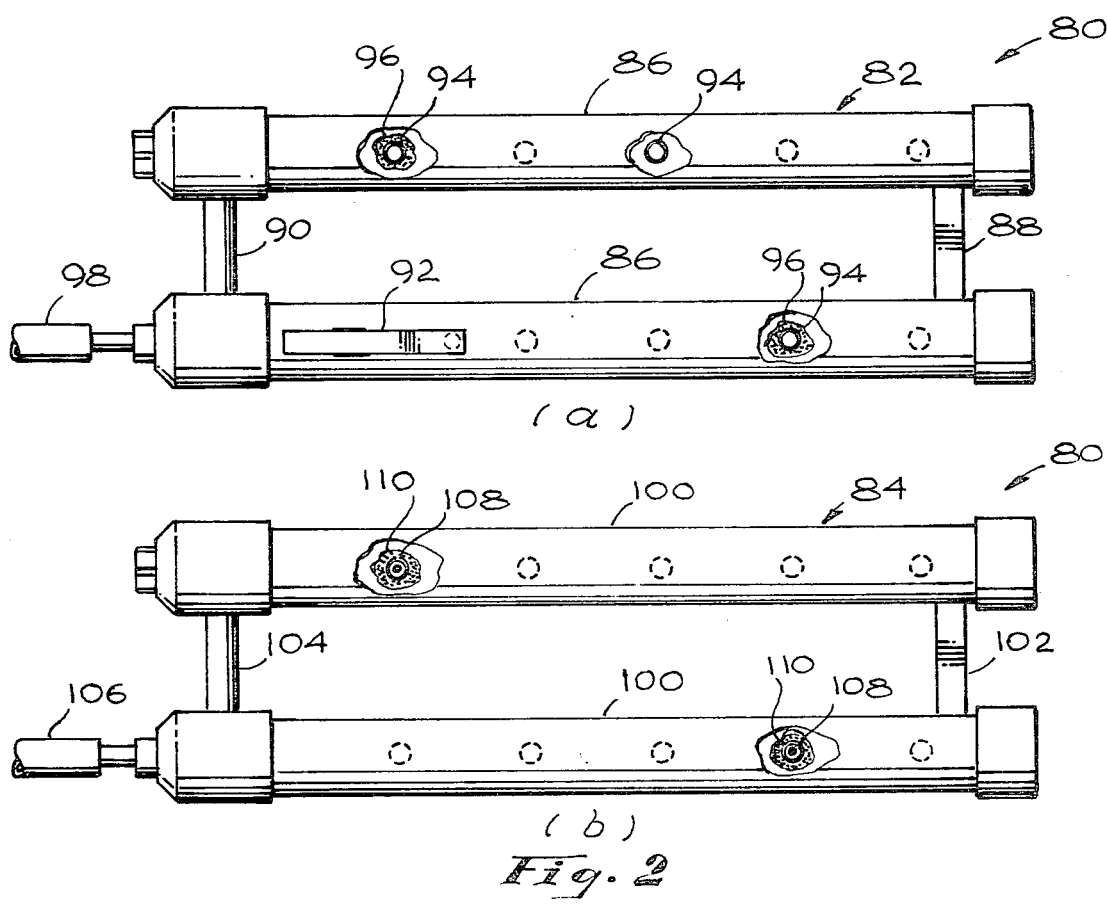

RAPID ASPIRATION SYSTEM FOR CULTURE MEDIA

BACKGROUND OF THE INVENTION

1. Field of the Invention

The present invention generally relates to culture media-treating apparatus and more particularly to hand-manipulatable aspirating equipment for removal of culture media.

2. Prior Art

The method normally used to feed cultures in petri dishes or the like reservoirs is relatively slow. Each such dish must be handled separately. The technician must lift the lid of each dish in turn to allow him to remove the old culture medium inside the dish. He then replaces it with fresh culture medium in order to feed the culture in the dish. Several hundred dishes have been considered to be the maximum daily number which can be handled by one technician utilizing this procedure. Not only is this procedure slow but there is also a substantial contamination danger because each dish must be handled by the technician several times for each feeding. Accordingly, there is a need for improved apparatus which will permit more rapid feeding of cultures grown in a plurality of covered dishes or the like and which at the same time will reduce the danger of contamination of and from those cultures.

SUMMARY OF THE INVENTION

The present invention satisfies the foregoing needs. The invention is substantially as set forth in the Abstract above. It is capable of rapidly and simultaneously treating a plurality of petri dishes or other reservoirs containing media-fed cultures so as first to remove the covers of the reservoirs simultaneously and then simultaneously aspirate the old media therefrom, whereupon new media can be sequentially or simultaneously added thereto, and then the covers can then be replaced simultaneously.

The system of the invention comprises a pair of hand manipulatable manifolds, one for each hand. One of the manifolds includes a plurality of spaced suction cups, while the other of these manifolds includes a plurality of aspirating pipettes. The cups and pipettes preferably are of equal number and disposed in the same pattern. The cups are capable of simultaneously lifting the covers or lids from a plurality of reservoirs such as petri dishes, so that the pipettes can aspirate the media simultaneously from the uncovered reservoirs. After filling the reservoirs with fresh media, the lids can be simultaneously replaced using the manifold which still holds them. One technician can quickly go from one set of reservoirs to the next, aspirating and replacing the media in as many as 1,200 dishes in a morning with ease. Since each lid is only removed once during each feeding and is in any event held by a suction cup on the appropriate manifold, there is a very low contamination rate when this system is used. The parts required for the system are easily obtained, can easily be sterilized and reused and are durable and inexpensive. Further advantages are set forth in the following detailed description and accompanying drawings.

DRAWINGS

FIG. 1 is a schematic side elevation, partly broken away, of a first preferred embodiment of the improved system of the present invention, the suction cup-containing manifold thereof being shown in FIG. 1a and the pipette-containing manifold thereof being shown in FIG. 1b; and, FIG. 2 is a schematic top plan view, partly broken away, of a second preferred embodiment of the improved system of the present invention, the suction cup-containing manifold thereof being shown in FIG. 2a and the pipette-containing manifold thereof being shown in FIG. 2b.

DETAILED DESCRIPTION

FIG. 1

Now referring more particularly to FIG. 1 of the accompanying drawings, a first preferred embodiment of the improved system of the present invention for culture media aspiration is shown schematically in side elevation. Thus, system 10 is shown which includes a pair of manifolds, namely manifold 12 of FIG. 1a, and manifold 14 of FIG. 1b. Manifold 12 comprises a hollow tubular elongated pipe 16 sealed at one end with a cap 18 and fitted at the opposite end with a connector 20 in which is inserted removable suction tubing 22 leading to a source of suction (not shown). Pipe 16 is hollow and the bottom thereof contains a plurality of openings 24 spaced along the length thereof, within which openings are fitted stubs 26 of hollow tubular piping extending outwardly (downwardly) from pipe 16, as shown in FIG. 1a. Thus, stubs 26 may vertically depend from horizontally extending pipe 16. Pipe 16 may be ceramic, plastic or metal, such as aluminum, steel, copper or the like with stubs 26 permanently secured thereto and preferably of the same or similar material. The outer or free end 28 of each stub 26 is provided with a suction disc or cup 30 of plastic, rubber or the like flexible material containing a central aperture 32 extending vertically therethrough into communication with openings 34 in stubs 26. Openings 34 lead to the hollow interior of pipe 16.

A portion of pipe 16 may be used as a handle 36 and includes on the upper surface thereof suction-relieving means comprising an opening 38 extending into the interior of pipe 16 and releasably covered by a closure plate 40 biased into the closed position by a spring 42 which is also connected to a support 44 secured to the top of pipe 16. Plate 40 is hand moveable into the open position to expose opening 38, all while manifold 12 is being held by handle 36.

Manifold 14 is of similar construction to manifold 12 in that it comprises an elongated pipe 50 of plastic, metal or ceramic or the like capped at one end by cap 52 and provided at the opposite end with a connector 54 and suction tubing 56 leading to a source of suction (not shown). Pipe 50 is hollow and has a plurality of openings 58 in the bottom thereof spaced along the length thereof and from which depend a plurality of spaced tubes 60, preferably of flexible rubber or the like, to the lower ends 62 of which are removably fitted 62 depending pipettes 64.

In operation, manifold 12 is first used to simultaneously remove the covers or lids 46 from five petri dishes or the like reservoirs. In order to do this, opening 38 is left closed, and suction is applied through tube 22 to manifold 12. Suction cups 30 are made to contact the upper surface of all five petri dish covers 46 while manifold 12 is being held by handle 36. Once suction cups 30 securely grip covers 46, an upward movement of manifold 12 lifts all five covers 46 simultaneously from petri dishes 48. While covers 46 are being held away from dishes 48 by manifold 12, manifold 14, which is held in the other hand of the technician, is brought over petri dishes 48 so that pipettes 64 dip into media 66 in dishes 48. Suction is applied to pipettes 64 through opening 58, pipe 50 and tubing 56 to draw media 66 up into and out pipettes 64, pipe 50 and tubing 56 for disposal. This occurs simultaneously with all five petri dishes contacted. Manual or automatic filling apparatus (not shown) can then be utilized to provide fresh culture media 66 to each of the five dishes 48. For example, the technician can temporarily lay manifold 14 down and use that hand to fill dishes 48 with the fresh media, as per filling apparatus which can, for example, have the general configuration of manifold 14, if desired. Pressure thus can force the fresh media into dishes 48. When dishes 48 are properly filled, manifold 12 which is still held in the opposite hand, can then be used to reapply covers 46 to dishes 48. The suction in manifold 12 is then relieved by opening aperture 38 by means of plate 40, so that the grip of cups 30 on covers 46 is broken and manifold 12 can then be retracted without lifting any of covers 46. Thus, the filling operation is complete.

Each of manifolds 12 and 14 can, for example, be easily and inexpensively fabricated of ½" I.D. copper or plastic tubing or the like having ¼" I.D. stubs and standard glass pipettes of proper size. Various other arrangements of components can also be made.

FIG. 2

FIG. 2 shows in top plan view a modified form of the system of FIG. 1. The only difference between the system of FIG. 2 and that of FIG. 1 is that the two manifolds shown in FIG. 2 each comprise a pair of elongated pipes joined in spaced side-by-side relation. Thus, system 80 includes manifolds 82 and 84. Manifold 82 is identical to manifold 12 except that it includes a pair of pipes 86 in tandem array interconnected by a bracket 88 and a hollow connector tube 90. Only one of pipes 86 contains a suction-relieving means 92 similar to opening 38, plate 40, spring 42 and support 44 of FIG. 1. Stubs 94 in the bottom of both pipes 86 have suction cups 96 attached thereto in the same manner as cups 30 depend from stubs 26. There are five stubs 94 in each of pipes 86, some of which are shown in phantom outline. A suction line 98 leads from one end of one pipe 86 while the other ends of these two pipes are sealed.

Manifold 84 is identical to manifold 14 except that it includes a pair of pipes 100 in tandem array interconnected by a bracket 102 at one end and a hollow connector tube 104 at the opposite end. One of the two pipes 100 is sealed at both ends while the other of the two pipes is sealed at one end and provided with a suction line 106 at the opposite end. The bottom of each pipe 100 is supplied with 5 spaced suction conduits comprising depending tubes 108 to the lower ends of which are releaseably fixed pipettes 110, similar to pipettes 64. The position of tubes 108 and pipettes 110 as shown in part in phantom outline in Section 2b.

System 80 is operated in the same manner as system 10. In this regard, manifold 82 is used to remove the covers or lids (not shown) of 10 petri dishes or other culture media-containing reservoirs (not shown) simultaneously. Manifold 82 is best gripped in the area of means 92 so that it can be operated at the appropriate time. Manifold 84 can be gripped along the length of either one of pipes 100. System 80 has the advantages of system 10 while providing for the rapid and simultaneous removal of culture media from 10 reservoirs arranged in a gridlike pattern corresponding to the placement of cups 96 and pipettes 110. It will be understood that pipettes 110 are spaced in the same arrangement as cups 96. The manifolds utilized in the present system can be constructed in various other physical arrangements and can contain various numbers of suction cups and pipettes corresponding to the configuration of the reservoirs to be simultaneously treated. Various other modifications, changes, alterations and additions can be made in the present system and in the components and parameters thereof. All such modifications, changes, alteration and additions which are in the scope of the appended claims form part of the present invention.

What is claimed is:

1. Improved rapid portable system for culture media aspiration, said system comprising, in combination:
   a. a first hand-manipulatable portable manifold comprising a elongated tubular hollow housing, and a plurality of stubs connected to said housing at spaced intervals and extending outwardly from said housing, and defining a plurality of openings communicating with the interior of said housing, said stubs having at their free outer ends suction cups with central openings therein communicating with said stub openings, said manifold also including suction means and suction-relieving means connected to said housing for delivery of suction to said cups; and,
   b. a second hand-manipulatable portable manifold having a hollow elongated tubular housing and a plurality of aspiration conduits of equal number and spatial orientation to said stubs and connected to said housing at spaced intervals, said conduits extending outwardly from said housing, said manifold including suction means communicating through said housing with said aspiration conduits for aspirating culture media.

2. The improved system of claim 1 wherein said housing of said first manifold includes a hollow handle and wherein both said suction means and said suction-relieving means are connected to said handle for manual operation and for easy manipulation.

3. The improved system of claim 2 wherein said suction-relieving means includes an opening in said handle and means for manually releasably sealing said opening while holding said handle.

4. The improved system of claim 1 wherein said aspiration conduits of said second manifold comprise removable pipettes and said housing of said second manifold includes a hollow handle.

5. The improved system of claim 1 wherein both said manifolds comprise tubing extending in an identical grid pattern so as to be capable of simultaneously aspirating a plurality of culture media reservoirs disposed in that grid pattern.

* * * * *